(12) United States Patent
Karas

(10) Patent No.: US 6,242,640 B1
(45) Date of Patent: Jun. 5, 2001

(54) TERTIARY ALKYL ESTER PREPARATION USING LARGE-PORE ZEOLITE CATALYSTS

(75) Inventor: Lawrence J. Karas, West Chester, PA (US)

(73) Assignee: ARCO Chemical Technology, L.P., Greenville, DE (US)

( * ) Notice: Subject to any disclaimer, the term of this patent is extended or adjusted under 35 U.S.C. 154(b) by 0 days.

(21) Appl. No.: 09/414,371

(22) Filed: Oct. 7, 1999

(51) Int. Cl.$^7$ .................................................. C07C 69/54
(52) U.S. Cl. ..................... 560/205; 560/241.1; 560/247
(58) Field of Search ................................. 560/247, 241.1, 560/205

(56) References Cited

U.S. PATENT DOCUMENTS

| | | |
|---|---|---|
| 2,678,332 | 5/1954 | Cottle et al. . |
| 3,031,495 | 4/1962 | Young et al. . |
| 3,172,905 | 3/1965 | Eckert . |
| 3,173,943 | 3/1965 | Hess et al. . |
| 3,492,341 | 1/1970 | Trevillyan . |
| 3,678,099 | 7/1972 | Kemp . |
| 4,365,084 | 12/1982 | Young . |
| 4,461,729 | 7/1984 | Young . |
| 4,465,852 | 8/1984 | Sato . |

OTHER PUBLICATIONS

"Introduction to Zeolite Science and Practice" van Bekkum et al. Elsevier (1991) p. 19.

Primary Examiner—Paul J. Killos
Assistant Examiner—Robert W. Deemie
(74) Attorney, Agent, or Firm—William C. Long

(57) ABSTRACT

A tertiary olefin such as isobutylene is reacted with a lower unsaturated carboxylic acid to produce the ester in the presence of a large pore zeolite catalyst such as Zeolite Y, Zeolite beta or Zeolite X, the reaction can be illustrated by the equation

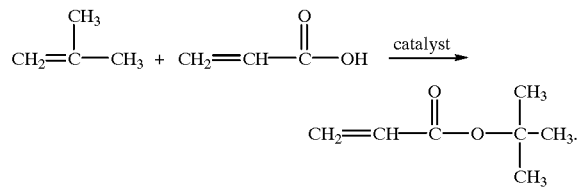

7 Claims, No Drawings

TERTIARY ALKYL ESTER PREPARATION USING LARGE-PORE ZEOLITE CATALYSTS

BACKGROUND OF THE INVENTION

1. Field of the Invention

The present invention provides an improved method for the preparation of esters of unsaturated acids such as t-butyl acrylate by reaction of a tertiary olefin with unsaturated acid in the presence of a large pore zeolite catalyst such as Zeolite Y, Zeolite X or Zeolite beta.

2. Description of the Prior Art

It is known to produce esters by the reaction of an olefin such as isobutylene with a lower carboxylic acid over a sulfonate group-containing cation exchange resin. See U.S. Pat. No. 3,678,099 and the references disclosed therein including U.S. Pat. Nos. 2,678,332, 3,031,495, 3,172,905 and 3,173,943.

A problem which is encountered in such prior procedures has been the tendency for polymerization of the olefin and/or acid where an unsaturated acid is used to occur during the esterification which results both in significant yield losses and in the formation of products such as olefin dimer which are difficult to separate from the product ester.

Problems of diisobutylene formation can be substantially overcome through the use of a selectivity enhancing modifier such as tertiary butanol. However, although the use of such a modifier has striking advantages, its use entails additional processing costs and purification procedures.

Other processes are described. For example, U.S. Pat. No. 3,492,341 describes the reaction of isobutylene with acetic acid to form ester using a mordenite aluminosilicate catalyst.

U.S. Pat. No. 4,365,084 describes ester production by reaction of a linear or slightly branched olefin with acetic acid using a catalyst such as HZSM-5. The use of olefins having unsaturation at the number 2 carbon atom is excluded.

U.S. Pat. No. 4,461,729 is similar to U.S. Pat. No. 4,365,084 and contains the additional step of hydrolyzing the ester to form secondary alcohol.

U.S. Pat. No. 4,465,852 relates to ester preparation by reaction of olefin with acetic acid. Although a great number of olefins are mentioned, including isobutylene, and a great number of catalysts are mentioned, including ZSM-5, the olefins exemplified are ethylene and propylene and the claims are limited to ethylene, propylene and butylene.

Copending patent application Ser. No. 09/022,183 filed Feb. 11, 1998 describes ester preparation by reaction of an olefin such as isobutylene with acetic acid using a ZSM-5 catalyst. Data are presented indicating that at the reported conditions of the testing, poor results were achieved with large pore zeolite catalyst, Zeolite beta.

BRIEF DESCRIPTION OF THE INVENTION

In accordance with the invention, olefin and lower unsaturated carboxylic acid are reacted in the presence of a large pore acidic zeolite such as Zeolite Y, Zeolite X, or Zeolite beta at conditions where the unsaturated ester is formed at high rates and selectivity, and whereby the formation of olefin, unsaturated acid and unsaturated ester polymerization products are maintained at a very low level.

DETAILED DESCRIPTION

The present invention is applicable to the formation of esters having the formula

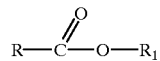

wherein $R_1$ is a $C_4$ or $C_5$ tertiary alkyl group and R is $CH_2$=CH— or

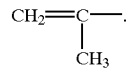

T-butyl acrylate or methacrylate are especially preferred products.

In accordance with the invention, olefin and the unsaturated organic carboxylic acid are reacted in the liquid phase to form ester over a solid acidic large pore size zeolite catalyst. The large pore zeolites used in accordance with the invention are those having twelve-ring pores as described, for example, at page 19 of "Introduction to Zeolite Science and Practice", van Bekkum et al. Elsevier (1991). Zeolite Y is especially useful as is Zeolite beta and Zeolite X. The zeolites employed are suitably made with conventional binders, eg. alumina, silica, and the like. As is well known, the acidic zeolite form is the hydrogen zeolite form, that is, the form in which the predominance and preferably all sodium is replaced by hydrogen is through acidification.

The conditions at which the esterification reaction is carried out are exceedingly important. The large pore acidic zeolites are extremely active catalysts and unless certain reaction conditions are employed, excessive amounts of olefin polymer are obtained.

The esterification reaction is carried out at pressures sufficient to maintain the liquid phase, usually 50 psig or higher. The upper pressure limit is governed largely by practical considerations, little is to be gained by operating at pressures in excess of 800 psig. Operation at 250–500 psig is generally preferred.

Reaction temperature is important, temperatures of about 20 to 80° C. are suitable, temperatures of about 35 to 50° C. are preferred.

Excessive contact times, especially at the higher temperature ranges are to be avoided. Reactant liquid weight hourly space velocities (WHSV) of about 10–100 $hr^{-1}$, preferably 25 to 50 $hr^{-1}$ are employed. These figures are based on the large pore zeolite content of the catalyst contact solid.

The mol ratio of olefin to unsaturated carboxylic acid can vary widely, ratios of 0.1–10 mols olefin per mol carboxylic acid are generally useful, ratios of 0.125 to 0.5 mols olefin per mol carboxylic acid are especially useful. The higher amounts of acid relative to olefin improve reaction selectivity and further aid in suppressing dimer make.

Where a selectivity enhancing modifying agent such as described in copending application Ser. No. 08/816,704 filed Mar. 13, 1997 is used, reaction conditions outside the above ranges can be used. For example, higher temperatures and longer contact times can be employed as can higher olefin to carboxylic acid ratios where the modifier is used. For example, reaction temperatures in the upper part of the 20–80° C. range can be used and liquid hourly space velocities below 10 $hr^{-1}$, eg. as low as 4 $hr^{-1}$ can be used where a selectivity enhancing modifier is used.

Especially preferred selectivity enhancing modifiers, where one is used, are t-butyl alcohol, t-amyl alcohol and the lower ($C_1$–$C_3$) alkyl ethers thereof such as methyl tertiary butyl ether, methyl tertiary amyl ether, and the like. Where used, at least 1 wt % of modifier based on the feed is used up to about 50 wt %.

The following example illustrates the invention:

An esterification run was carried out using large pore zeolite catalyst and reacting isobutylene and acrylic acid to form t-butyl acrylate. The run was carried out at 500 psig and about 40° C. The mol ratio of acrylic acid to isobutylene in the feed was 7:1 and acidic Zeolite Y diluted with 3 parts alumina per part Zeolite Y was used as catalyst. Space velocity was 23 $hr^{-1}$ based on Zeolite Y and 84% isobutylene conversion was achieved. The product was primarily t-butyl acrylate, very little polmer product was formed.

We claim:

1. In the reaction of a $C_4$ or $C_5$ olefin with an unsaturated lower carboxylic acid in the presence of a solid acidic catalyst to form product ester, the improvement which comprises carrying out the reation in the presence of a large pore acidic zeolite having twelve-ring pores at the following conditions:

a) temperature in the range of about 20–80° C.,
b) liquid hourly space velocity (WSHV) in the range of about 10–100 $hr^{-1}$,
c) olefin to acid feed mol ration of about 0.1–10 mols olefin per mol acid,
d) pressure sufficient to maintain the liquid phase.

2. The process of claim 1 wherein the olefin is isobutylene.

3. The process of claim 1 wherein the carboxylic acid is acrylic acid.

4. The process of claim 1 wherein the solid acidic catalyst is Zeolite beta.

5. The process of claim 1 wherein the solid acidic catalyst is Zeolite X.

6. The process of claim 1 wherein the solid acidic catalyst is Zeolite y.

7. The process of claim 1 wherein a selectivity enhancing modifier is used and wherein WSHV is in the range 4–100 $hr^{-1}$.

* * * * *